(12) United States Patent
Honold et al.

(10) Patent No.: US 7,008,764 B1
(45) Date of Patent: Mar. 7, 2006

(54) OPTIMIZATION OF CELLS FOR ENDOGENOUS GENE ACTIVATION

(75) Inventors: Konrad Honold, Penzberg (DE); Thomas Holtschke, München (DE); Anne Stern, Penzberg (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/203,500

(22) Filed: Dec. 1, 1998

(30) Foreign Application Priority Data

Dec. 1, 1997 (EP) ............................................ 97121075

(51) Int. Cl.
*C12Q 1/68* (2006.01)

(52) U.S. Cl. ........................ 435/6; 435/320.1; 435/455; 536/23.1; 536/24.1

(58) Field of Classification Search .................... 435/6, 435/320.1, 455; 536/23.1, 24.1
See application file for complete search history.

(56) References Cited

U.S. PATENT DOCUMENTS

| 4,959,317 A | | 9/1990 | Sauer | |
|---|---|---|---|---|
| 5,434,066 A | * | 7/1995 | Bebee et al. | ................. 435/462 |
| 5,695,977 A | * | 12/1997 | Jurka | ....................... 435/172.3 |
| 6,020,144 A | * | 2/2000 | Gueiros-Filho et al. | ..... 435/7.22 |
| 6,130,364 A | * | 10/2000 | Jakobovits et al. | ............ 800/6 |

FOREIGN PATENT DOCUMENTS

| EP | 0 220 009 | | 4/1987 | |
|---|---|---|---|---|
| EP | 0 343 783 A2 | | 11/1989 | |
| EP | 0 747 485 A1 | | 12/1996 | |
| EP | 0 747 485 | | 12/1996 | |
| EP | 0747485 A1 | | 12/1996 | |
| WO | 90/11354 | | 10/1990 | |
| WO | WO 90/11354 | | 10/1990 | |
| WO | 91/09955 | | 7/1991 | |
| WO | WO 91/09955 | | 7/1991 | |
| WO | WO 91/09955 A | | 7/1991 | |
| WO | 92/15694 | | 9/1992 | |
| WO | WO94/12650 | * | 6/1994 | ................ 435/69.4 |
| WO | 94/17176 | | 8/1994 | |
| WO | WO 94/17176 A | | 8/1994 | |
| WO | 96/29411 | | 9/1996 | |
| WO | WO 96/29411 A | | 9/1996 | |
| WO | WO 96/29411 | | 9/1996 | |
| WO | 96/30498 | | 10/1996 | |
| WO | WO 96/30498 A | | 10/1996 | |
| WO | WO 96/39426 | | 12/1996 | |
| WO | WO97/37012 | * | 10/1997 | ................ 435/455 |

OTHER PUBLICATIONS

Cruz et al. Double targeted gene replacement for creatioging null mutants. PNAS vol. 88:7170–7174, Aug. 1991.*
Cruz et al. Gen replacement in parasitic protozoa. Nature vol. 348:171–173, Nov. 8, 1990, sent in previous action.*
Mazure et al. Oncogenic transformation and hypoxia synergistically act to modulate vascular endothial growth factor expression. Cancer Research. vol. 56:3436–3440, Aug. 1996.*
Gu et al., "Independent Control of Immunoglobulin Switch Recombination at Individual Switch Regions Evidenced through Cre–IoxP–Mediated Gene Targeting", CELL, vol. 73, 1155–1164, Jun. 19, 1992.
Database WPI, Section CH, Week 198801 Derwent Publications Ltd., & JP 62 265922 A, Nov. 18, 1987.
Fukushige et al., Genomic Targeting with a Positive–Selection LOX Integration Vector Allows . . . , Proceedings of the National Academy of Science of USA, Vo. 89, No. 17, Sep. 1, 1992, pp. 7905–7909.
Wang et al., "High Frequency Recombination Between LOXP Sites in Human Chromosomes Mediated . . . ", Somatic Cell and Molecular Genetics, vol. 21, No. 6, Nov. 6, 1995, pp. 429–441.
Semenza, et al., "A Nuclear Factor Induced by Hypoxia via De Novo Protein Synthesis binds to the Human Erythropoietin Gene Enhancer at a Site Required for transcriptional Activation", Molecular and Cellular Biology, Dec. 1992, vol. 12, No. 12, pp. 5447–5454.
Wang, et al., "General involvement of hypoxia–inducible factor 1 in transcriptional response to hypoxia", Proc. Natl. Acad. Sci., USA, vol. 90, pp. 4304–4308, May 1993.
Dachs, et al., "Targeting gene expression to hypoxic tumor cells", Nature Medicine, vol. 3, No. 5, May 1997, pp. 515–520.

(Continued)

Primary Examiner—James Ketter
(74) Attorney, Agent, or Firm—Rothwell, Figg, Ernst & Manbeck, P.C.

(57) ABSTRACT

The invention concerns a process for optimizing the gene expression in cells. A first aspect concerns a process for changing the expression of a nucleic acid sequence which is present endogenously in a eukaryotic cell by introduction of a heterologous expression control sequence into the genome of the cell by means of homologous recombination as well as site-specific recombinase-mediated excision of inserted foreign DNA and its replacement by further heterologous expression control sequences or/and amplification genes. In addition the invention concerns the introduction of one or several nucleic acid sequences to which an activator protein or an activator protein complex binds e.g. a hypoxia-inducible factor (HIF), into the genome of a eukaryotic cell by homologous recombination in order to change the expression of a target gene. Furthermore the invention concerns a process for testing the influence of 5' or 3' non-coding nucleic acid fragments on the expression of a target gene by determining the expression of a reporter gene. In addition the invention concerns a process for providing a DHFR-negative eukaryotic cell containing a recombinase target sequence as well as the expression of a nucleic acid sequence inserted into the recombinase target sequence.

24 Claims, 6 Drawing Sheets

OTHER PUBLICATIONS

Damert, et al., "Activator–protein binding potentiates the hypoxia–inducible factor–1–mediated hypoxia–induced transcriptional activation of vascular–endothelial growth factor expression in C6 glioma cells", Biochem. J., (1997) 327, pp. 419–423.

Tian et al., "Endothelial PAS domain protein 1 (EPAS1), a transcription factor selectively expressed in endothelial cells", Genes and Development, vol. 11, No. 1, Jan. 1997, pp. 72–82.

Database WPI, JP 62 265992 A, Derwent Publication Ltd., Nov. 1997.

Semenza, et al., "Transcriptional Regulation of Genes Encoding Glycolytic Enzymes by Hypoxia–inducible Factor 1", The Journal of Biological Chemistry, vol. 269, No. 38, Sep. 1994, pp. 23757–23763.

"General involvement of hypoxia–inducible factor 1 in transcriptional response to hypoxia" Wang et al. Proc. Natl. Acad. Sci. vol. 90, pp. 4304–4308, May 1993.

"Targeting gene expression to hypoxic tumor cells", Dachs et al., Nature Medicine, vol. 3, No. 5, May 1997.

Li et al., Proc. Natl. Acad. Sci., vol. 93, Jun. 1996, pp. 6158–6122 "Generation of mice with 1–7 a 200–kb amyloid precursor protein gene deletion by Cre recombinase–mediated site specific . . . ".

Baubonis et al., Nucleic Acids Research, vol. 21, No. 9, May 11, 1993, pp. 2025–2029, "Genomic Targeting with purified CRE recombinase".

Metzger et al., Proceedings of the National Academy of Sciences of USA, vol. 92, No. 15, Jul. 18, pp. 6991–6995, "Conditional site–specific recombination in mammalian cells . . . ".

Merrihew et al., Somatic Cell and Molecular Genetics, vol. 21, No. 5, Sep. 1995, pp. 299–307, "Efficient modification of the APRT gene by FLP/FRT site–specific targeting".

Fukushige et al., Proc. of the National Academy of Sciences of USA, vol. 89, No. 17, Sep. 1, 1992, pp. 7905–7909, "Genomic Targeting with a positive selection lox integration . . . ".

* cited by examiner

Fig.6
A. pND1 (11.5kb)
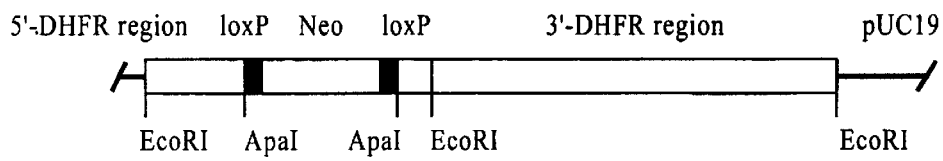
B. pHD1 (12.3kb)
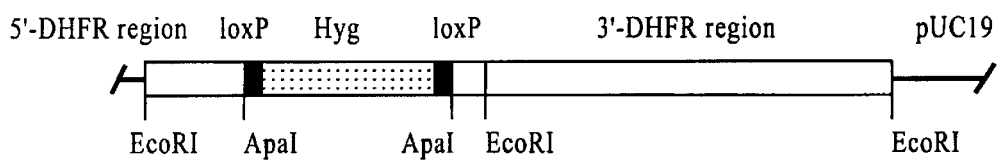
Fig.7
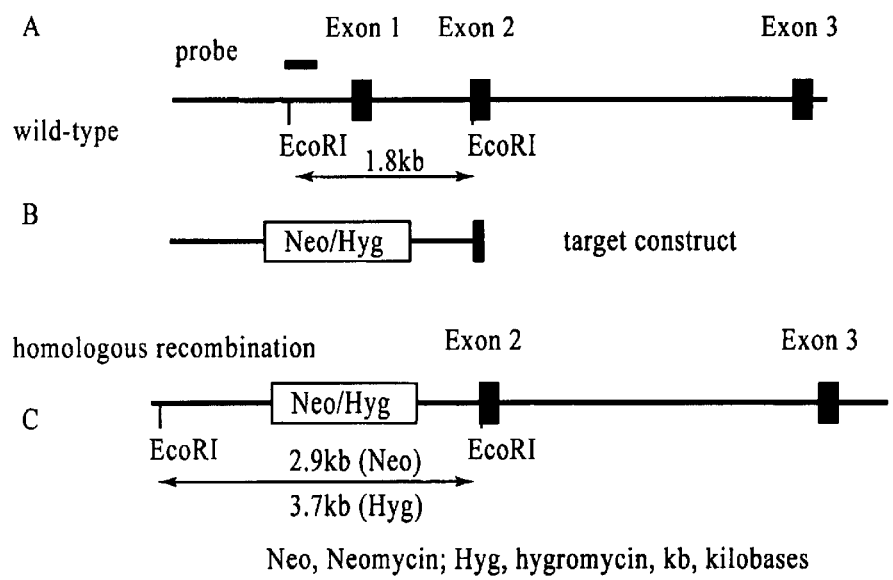
Neo, Neomycin; Hyg, hygromycin, kb, kilobases
Fig.8
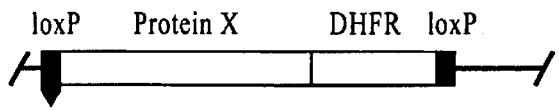

US 7,008,764 B1

OPTIMIZATION OF CELLS FOR ENDOGENOUS GENE ACTIVATION

The invention concerns a process for optimizing gene expression in cells. A first aspect concerns a process for changing the expression of a target gene that is present endogenously in a eukaryotic cell by introducing a heterologous expression control sequence or/and an amplification gene into the genome of the cell by means of homologous recombination and also concerns the excision of the inserted foreign DNA mediated by a site-specific recombinase and its replacement by other heterologous expression control sequences or/and amplification genes. The invention additionally concerns the introduction of one or several nucleic acid sequences to which an activator protein or an activator protein complex e.g. a hypoxia-inducible factor (HIF) binds, into the genome of a eukaryotic cell by homologous recombination in order to change the expression of a target gene. Furthermore the invention concerns a method for testing the influence of non-coding nucleic acid fragments on the 5' side or 3' side on the expression of a target gene by determining the expression of a reporter gene. In addition the invention concerns a process for preparing a DHFR-negative eukaryotic cell containing a recombinase target sequence as well as the expression of a nucleic acid sequence inserted into the recombinase target sequence.

Gene expression in a cell can take place constitutively for example in so-called housekeeping genes or be regulated. Regulated expression is particularly necessary for genes which only have to be expressed in a particular development stage of the cell or when there is a change in the environmental conditions.

Expression is regulated at the transcription level by the promoter that is operatively linked with the coding nucleic acid sequence the activity of which can be controlled by repressors and activators. Binding of repressors or activators to non-coding nucleic acid sequences of the gene can reduce or increase the activity of the promoter (L. Stryer, Biochemie, Chapter 12, "Spektrum der Wissenschaft, Verlagsgesellschaft", Heidelberg, 1990). The amount of repressors or activators that are contained in a cell is in turn regulated by factors such as for example environmental conditions. Hypoxia-inducible factors (HIF) are an example of activators which are induced by reduced $O_2$ supply and lead to an increased expression of the erythropoietin gene (Blanchard K. L. et al., Hypoxic induction of the human erythropoietin gene: Cooperation between the promoter and enhancer, each of which contains steroid receptor response elements, (1992), Mol. Cell. Biol. 12, 5373–5385; Wang G. L. and Semenza G. L., Characterization of hypoxia-inducible factor 1 and regulation of DNA binding activity by hypoxia, (1993), J. Biol. Chem., 268, 21513–21518; Wang G. L. et al., Hypoxia-inducible factor 1 is a basic-helix-loop-helix-PA heterodimer regulated by cellular $O_2$ tension, (1995), Proc. Natl. Acad. Sci. USA, 92, 5510–5514).

Furthermore the amount of an expressed protein depends on the stability of the mRNA. Recognition sequences for mRNA degrading enzymes are located in the 3' region of an mRNA which influence the stability of the mRNA and thus the expression level (Shaw G. and Kamen, R., A Conserved AU Sequence from the 3'Untranslated Region of GM-CSF mRNA Mediates Selective mRNA Degradation, Cell (1986), 659–667). In this connection the half-life of the mRNA correlates with the amount of expressed protein. A third level of expression regulation is translation.

Hence the expression of a gene is subject to complex regulation mechanisms which can differ greatly in individual cases.

Proteins can be obtained with the aid of recombinant DNA technology which utilizes knowledge on expression regulation (Sambrook et al., 1989, Molecular Cloning, A Laboratory Manual, Cold Spring Harbor). Vectors are used for this which contain a nucleic acid sequence coding for the corresponding protein under the control of a suitable promoter as well as additional sequences that are necessary to express the protein and replicate the vector. The vector is then introduced into a host cell by means of known methods, the cell is cultured and the By recombinant protein can be isolated from the cell or the culture medium.

Prokaryotic or eukaryotic cells can be used as the host cell. Prokaryotic cells, in particular E. coli cells, are unproblematic to handle but have a number of disadvantages when eukaryotic proteins are expressed recombinantly.

Prokaryotes and eukaryotes differ in the expression processing path, in the cell medium conditions, as well as in the chaperones involved in protein processing. Hence a eukaryotic protein produced in a prokaryote may differ decisively from the corresponding native protein.

For example the protein folding pattern and the activity of the protein may be modified. Also proteins in a prokaryotic host cell are usually not glycosylated. However, a correct glycosylation pattern is a crucial characteristic in many cases for the effectiveness and tolerance for example in the production of proteins for a pharmaceutical formulation.

Glycosylated proteins are therefore produced by means of eukaryotic host cells or cell lines, for example CHO (Chinese Hamster Ovary) cells. Despite the use of eukaryotic cells, changes in the recombinantly produced protein can occur due to species differences for example when expressing a human protein in non-human cells which is why this method is unsuitable for many applications.

For the recombinant production of proteins, host cells are transiently or stably transfected with expression vectors, stably transfected cells being used in particular for large scale production processes.

Unspecific, random integration of the expression vector sequences into the genome of the host cell can lead to cells with a low production capacity or to unstable properties of the cells. For example the production output can decrease during the course of a production process or the ability of the cells to express the recombinant protein can be completely lost.

A method for increasing gene expression is gene amplification in which a nucleic acid sequence coding for a protein is coupled to an amplification gene. A multiplication of both sequences is achieved by a selection step which leads to an increased expression (Schimke, R. T. (Ed.) (1982), Gene amplification, Cold Spring Harbor Lab., Cold Spring Harbor, N.Y.).

A nucleic acid coding for a dihydrofolate reductase (DHFR) can for example be used as an amplification gene (Kaufmann R. J., Sharp P. A. (1982), Amplification and expression of sequences cotransfected with a modular dihydrofolate reductase complementary DNA gene, J. Mol. Biol. 159:601 ff).

A selection step carried out with methotrexate enables cells to be obtained which are resistant to methotrexate and contain in their genome the nucleic acid sequence coding for a DHFR and the nucleic acid sequence coupled thereto in a 20- to 50-fold amplification (R. Knippers, 1982, "Molekulare Genetik", Thieme, Stuttgart).

Such a gene amplification method is most effectively carried out with a DHRF-negative cell. JP-62265992 describes for example a human DHFR-negative cell.

However, it does not mention a site-specific integration of an expression vector by means of homologous recombination and amplification of these sequences in this cell.

Even when carrying out a gene amplification process the disadvantages described above such as instability of the cells can occur due to random integration of the expression vector into the genome of the cell.

It is only possible to avoid the described disadvantages when foreign DNA is site-specifically integrated at a selected gene locus by homologous recombination which leads to an endogenous gene activation. Corresponding methods are known and are called gene targeting (WO 90/11354; WO 91/09955). In this process the cell is transfected with a vector which contains a positive selection marker gene flanked by nucleic acid sequences which are homologous to a gene locus at which it is intended to integrate the vector into the genome of the cell. Between the homologous nucleic acid sequences there is additionally a heterologous expression control sequence in order to increase the expression of the target gene in the cell and optionally an amplification gene to increase the copy number of the target gene.

A disadvantage of previously known gene targeting methods is that it is often extremely laborious to produce cells with properties that enable the production of a desired protein in an adequate amount and quality for commercial purposes. In particular the selection of optimal expression control sequences or/and amplification genes for the expression of a desired target protein often requires a very large series of homologous recombination experiments which are extremely time-consuming due to the complicated procedure for isolating clones in which the desired recombination event has taken place.

Homologous recombination can also be used to switch off the expression of certain genes in a cell in order to carry out protein function studies. For this knockout mice are produced in which the gene coding for a protein to be examined is switched off by homologous recombination in embryonic stem cells. After carrying out additional process steps, mice are obtained that cannot express a functional protein from the start of their development due to the inactivation of both alleles of this gene (Thomas, K. R., Capecchi M. R., (1987), Site-directed mutagenesis by gene targeting in mouse embryo-derived stem cells, Cell 51: 503–512).

The Cre-Lox system can be used to tissue-specifically and time-specifically switch off a certain gene and to examine it. For this purpose a nucleic acid fragment flanked by two loxP sequences is introduced into the genome of a cell by homologous recombination and can subsequently be cleaved again from the genome by a Cre recombinase that is expressed in the cell (Sauer B, Henderson N (1989): Site-specific DNA recombination at loxP sites placed into the genome of mammalian cells. Nuc Acid Res 17:147–161; Sauer B., Henderson N. (1990), Targeted insertion of exogenous DNA into the eukaryotic genome by the Cre recombinase, New Biol. 5:441–449). The prior art makes no mention of using the Cre-lox system or another site-specific recombinase system for the site-specific integration of expression control sequences or amplification genes into the genome of eukaryotic cells in order to change endogenous gene expression.

The object of the present invention was to provide a new process for optimizing endogenous gene activation by homologous recombination which at least partially eliminates the disadvantages of the prior art.

This object is achieved by providing a new process and vector constructs which considerably simplify an optimization of the expression output of genes in eukaryotic cells. A first aspect of the invention concerns a process for changing the expression of a nucleic acid sequence which is present endogenously in a eukaryotic cell which is characterized in that (a) the cell is transfected with a first vector comprising
  (i) at least one sequence selected from a first heterologous expression control sequence and a first amplification gene,
  (ii) a positive selection marker gene,
  (iii) at least two target sequences for a site-specific recombinase flanking the sequences (i) and (ii),
  (iv) DNA sequences which flank the sequences (i), (i) and (iii) and are homologous to a nucleic acid section in the genome of the cell in order to allow a homologous recombination
(b) the transfected cell is cultured under conditions under which a homologous recombination of the vector takes place and
(c) the cell obtained according to step (b) is isolated.

A cell is provided by the process according to the invention which has an endogenous gene in operative linkage with a heterologous expression control sequence or/and an amplification gene and these sequences are flanked by target sequences for a site-specific recombinase e.g. the Cre recombinase. This cell is very well-suited for investigations on the optimization of the expression of the target gene since the presence of the target sequences for the site-specific recombinase enables a simple replacement of the first heterologous expression control sequence or/and the first amplification gene by a second heterologous expression control sequence or/and a second amplification gene.

The term "site-specific recombinase" according to the present invention encompasses proteins and protein complexes which mediate DNA rearrangements on a specific DNA target sequence including site-specific recombinases of the integrase or resolvase invertase classes (Stark et al., Trends Genet. 8 (1992), 432–439; Abremski and Hoess, Protein Engineering 5 (1992), 87–91; Khan et al., Nucleic Acids Res. 19 (1991), 851–860) and site-specific recombination mediated by intron-coded endonucleases (Perrin et al., EMBO J. 12 (1993), 2939–2947). Preferred recombinase proteins are selected from the group comprising the FLP recombinase of the $2\mu$ episome of *Saccharomyces cerevisiae* (e.g. Falco et al., Cell 29 (1982), 573–584; Cox, Proc. Natl. Acad. Sci. USA 80 (1983) 4223–4227; Konsolaki et al., New Biologist 4 (1992), 551–557), the Cre recombinase of the *E. coli* phage P1 (e.g. Sauer and Henderson (1989) supra), the R-recombinase from the *Zygosaccharomyces rouxii* plasmid pSR1 (Matsuzaki et al., J. Bacteriol. 172 (1990), 610–618), the A recombinase from the *Kluyveromyces drosophilarium* plasmid pKD1 (Chen et al., Nucleic Acids Res. 14 (1986), 4471–4481), the A recombinase from the *Kluveromyces waltii* plasmid pKW1 (Chen et al., J. Gen. Microbiol. 138 (1992), 337–345), a component of the λ-int recombination system (Landy, Annu Rev. Biochem. 5 (1989), 913–949) and a component of the gin recombination system of the phage $\mu$ (Klippel et al., EMBO J. 12 (1993), 1047–1057). In addition the fusion proteins described in the European Patent EP-B-0 707 599 composed of a site-specific recombinase and a nuclear receptor or the ligand-binding domain thereof are also suitable. Target sequences of the Cre recombinase i.e. loxP sequences are particularly preferably used for the process according to the invention.

In contrast to the recombinant production of proteins by site-unspecific integration of heterologous genes and their associated disadvantages, the process according to the invention utilizes the advantages of site-specific endogenous gene activation by homologous recombination.

A simplified selection of suitable combinations of heterologous expression control sequences and amplification genes enables optimized production clones with stable properties to be obtained with high probability which enable the production of a protein which substantially corresponds to the native protein with regard to its structure and activity.

The selection of suitable homologous sequences which flank the heterologous expression control sequence, the amplification gene, the positive selection marker gene and the recombinase target sequences is preferably carried out according to the methods described in WO90/11354 and WO91/09955.

In addition the homologous sequences may also contain modifications which lead to mutations in the expressed protein such as for example point mutations, insertions or/and deletions of individual amino acids or whole amino acid sections.

Thus the process according to the invention not only enables the expression level of an endogenous nucleic acid sequence to be changed in a single process step but also simultaneously enables the introduction of a mutation into the coding region of the endogenous nucleic acid sequence. Hence the process according to the invention is particularly advantageous for the production of proteins for pharmaceutical applications. Such proteins should have no further modifications compared to native proteins apart from mutations to increase the efficacy of the protein.

According to the invention it is possible to use any eukaryotic cell, preferably a mammalian cell, particularly preferably a human cell. The process according to the invention can be carried out with non-immortalized cells e.g. fibroblasts and also with immortalized cells e.g. tumour cell lines. Immortalized cells are preferred.

The solutions and media used to carry out the process according to the invention are preferably selected such that optimal conditions are present in the respective process step. The cells are cultured using media which contain all substances necessary for an adequate cell growth and are optionally buffered. It is preferable to use cells which can be cultured in serum-free medium. The cell used is particularly preferably a Namalwa, HT1080 or HeLa S3 cell.

The process according to the invention enables optimization of the expression of a nucleic acid sequence present endogenously in the cell i.e. of a target gene by selection of an optimal expression control sequence, an optimal amplification gene or/and by selection of an optimal combination of expression control sequence and amplification gene.

Any nucleic acid sequence can be used as the heterologous expression control sequence which influences the expression of the target gene after its integration into the genome of the cell. This includes nucleic acid sequences which can directly interact with transcription components such as transcription initiation factors or RNA polymerases and nucleic acid sequences whose influence on transcription is mediated by interactions with activators or repressors. The heterologous expression control sequence preferably contains a promoter/enhancer, particularly preferably viral promoters and most preferably a CPV promoter.

The heterologous expression control sequence can also include a 3' non-coding sequence. 3' non-coding sequences can have a stabilizing or destabilizing effect on an mRNA and thus increase or decrease its half-life. The introduction of a sequence that stabilizes an mRNA can increase the half-life of an mRNA and thus the yield of its encoded protein.

In a preferred embodiment an endogenous expression control sequence of the target gene is removed by the homologous recombination. This is particularly advantageous when the endogenous sequence contains a repressor-binding sequence. The expression can also be reduced by a 3' non-coding sequence which has a destabilizing effect on the mRNA which results in a decrease in the amount of translated protein.

In addition the process according to the invention allows the selection of an optimal amplification gene. The amplification gene is preferably used in an expressible form i.e. in operative linkage with a suitable promoter and is arranged in the vector such that after homologous integration of the vector into the genome of the eukaryotic cell it is located near to the target gene. Carrying out an amplification step leads to an increase in the number of copies of the target gene in the cell. This can result in a further increase in the expression of the endogenous nucleic acid sequence. Examples of suitable amplification genes are dihydrofolate reductase (DHFR), adenosine deaminase, ornithine decarboxylase or muteins of these genes. The amplification gene is preferably a DHFR gene or a mutated form thereof (Simonsen et al., Nucleic Acids Res. 1988, 16 (5): 2235–2246), especially in cells which contain an endogenous DHFR gene.

Any suitable resistance gene for a eukaryotic cell which leads to a selectable phenotype such as e.g. an antibiotic resistance can be used as a positive selection marker. The positive selection marker gene is preferably a neomycin, kanamycin, geneticin or hygromycin resistance gene. The positive selection marker gene is preferably used in an expressible form i.e. in operative linkage with a suitable promoter.

If a negative selection marker gene is used then a second negative selection step is usually carried out in addition to the positive selection step. The advantage of this is that, after carrying out the selection steps, the identified clones contain a lower proportion of false-positive clones i.e. vectors that are randomly integrated into the genome. The negative selection marker gene is preferably a thymidine kinase gene (TK) or/and a hypoxanthine-guanine-phosphoribosyl transferase gene (HGPRT).

As a result of the presence of the target sequences of the site-specific recombinase it is possible to cut out nucleic acid sequences located between these sequences from the genome of the cell using the site-specific recombinase. The nucleic acid sequence located between the target sequences is preferably cleaved from the genome by transient activation of the corresponding recombinase in the cell. This transient activation of the recombinase can for example be carried out by (a) transfecting the cell with a second vector containing a nucleic acid sequence coding for the recombinase operative linked with an expression control sequence that is active or can be activated in this cell and (b) culturing the cell transfected in this manner under conditions under which the recombinase is expressed and is active and (c) optionally isolating the cell.

If recombinaselnuclear receptor fusion proteins are used, the transient activation of the cell can also be carried out by the controlled addition of the ligand for the nuclear receptor.

After removing the DNA located between the target sequences, the remaining target sequence e.g. the loxP sequence can be used for additional process steps.

In a further preferred embodiment the process is characterized in that
(a) the cell is transfected with a third vector comprising
  (i) at least one sequence selected from a second heterologous expression control sequence and a second amplification gene
  (ii) a positive selection marker gene which preferably differs from the positive selection marker gene of the first vector and
  (iii) at least two recombinase target sequences flanking the sequences (i) and (ii)
(b) the transfected cell is cultured under conditions under which the sequence flanked by the target sequences is integrated into the target sequence in the genome of the cell
(c) the cell obtained according to step (b) is isolated and
(d) optionally steps (a) to (c) are repeated at least once with expression control sequences or/and amplification genes which vary in each case.

Hence the process according to the invention enables many expression control sequences, amplification genes or combinations of expression control sequences and amplification genes to be tested simply and rapidly. Hence it is not necessary to carry out a time-consuming and expensive site-specific integration for each individual heterologous expression control sequence and each individual amplification gene to determine an optimal expression/amplification system for each individual target gene.

The positive selection marker gene in a third vector preferably differs from that of a first vector in order to simplify the selection process and to minimize the number of false positive clones.

The recombinase target sequences in the vector used according to the invention can correspond to naturally occurring target sequences or optionally have mutations which do not impair the effectiveness of the site-specific recombinase.

A further subject matter of the invention is a vector for homologous recombination in particular for the site-specific introduction of recombinase target sequences into the genome of a cell comprising
(i) at least one sequence selected from an expression control sequence and an amplification gene,
(ii) a positive selection marker gene,
(iii) at least two target sequences for a site-specific recombinase which flank the sequences (i) and (ii),
(iv) DNA sequences flanking the sequences (i), (ii) and (iii) which are homologous to a nucleic acid section in the genome of a cell in order to allow a homologous recombination and
(v) optionally a negative selection marker gene.

In addition all vectors according to the invention preferably contain the necessary sequence elements for propagation and multiplication in suitable host cells such as origin of replication, selection marker genes etc.

Yet a further subject matter of the invention is a vector, in particular for introducing DNA into the genome of a cell by means of a site-specific recombinase system comprising
(i) at least one sequence selected from an expression control sequence and an amplification gene,
(ii) a positive selection marker gene and
(iii) at least two recombinase target sequences flanking the sequences (i) and (ii).

Yet a further subject matter of the present invention is a eukaryotic cell, preferably a human cell, which is obtainable by a process as described above. This cell, e.g. a human cell, is preferably characterized in that it
(a) contains at least one chromosomally located sequence selected from a heterologous expression control sequence and an amplification gene in operative linkage with a nucleic acid sequence that is present endogenously and
(b) this sequence is flanked by recombinase target sequences.

A further aspect of the present invention concerns a process for changing the expression of a nucleic acid sequence that is present endogenously in a eukaryotic cell which is characterized in that
(a) the cell is transfected with a vector comprising
  (i) at least one nucleic acid sequence that binds an activator protein e.g. a hypoxia-inducible factor (HIF),
  (ii) a positive selection marker gene,
  (iii) DNA sequences flanking the sequences (i) and (ii) which are homologous to a nucleic acid section in the genome of the cell in order to allow a homologous recombination,
(b) the transfected cell is cultured under conditions under which a homologous recombination of the vector takes place and
(c) the cell obtained according to step (b) is isolated.

Surprisingly the genomic integration of a nucleic acid sequence which binds one or several activator proteins (proteins which increase gene expression by binding to the nucleic acid sequence) in the region of the expression control sequence of a target gene in particular in its regulatory regions, does not reduce the expression of the target gene but in contrast it is possible by selection of suitable culture conditions to increase the expression of the endogenous target gene or to induce the expression of a non-expressed endogenous target gene.

Examples of suitable activator proteins are the hypoxia-inducible factors HIF-1α and HIF-1β as well as the interferon regulated factor 1 (IRF-1) which can increase transcription by binding to the interferon consensus sequence (ICE) (Tanaka N., Kawakami T., Taniguchi T., Mol. Cell. Biol. (1993), Aug; 13(8): 4531–4538).

After operatively linking one or several nucleic acid sequences, that bind a HIF or other activator proteins, to a target gene that is present endogenously, the expression of the target gene can be regulated by selecting suitable culture conditions. An advantage of this, especially for a commercial scale production, is that the expression of a protein can be induced at an optimal time for the production process. This is beneficial because the average residence time of the synthesis product in the culture medium supernatant is reduced. This also reduces the amount of undesired degradation products of the protein. This has a positive effect on the subsequent purification steps, reduces the production costs and leads to a qualitatively improved final product.

In order to carry out the process according to the invention it is sufficient to operatively link one or several activator-binding nucleic acid sequences with the target gene. Preferably two HIF-binding nucleic acid sequences are used. The HIF-binding nucleic acid sequence is particularly preferably selected from the 53 bp sequence according to sequence ID NO.1, the 43 bp sequence according to sequence ID NO.2, a sequence homologous to these sequences or a sequence hybridizing with these sequences under stringent conditions.

The use of two HIF-binding nucleic acid sequences surprisingly leads to a synergistic effect. This leads to a greater increase in the expression of endogenous nucleic acids than when using each of these sequences alone.

If necessary the expression of the activator protein which binds to the activator sequences introduced in the region of the target gene can be induced or/and increased in the cell. This can for example be achieved by transfecting the cell with a vector comprising
(i) a nucleic acid sequence coding for an activator protein which is operatively linked with an active expression control sequence in this cell and
(ii) optionally a positive selection marker gene.

Any nucleic acid sequence coding for an activator protein can be used whose expression product can bind to the activator-binding nucleic acid sequence integrated into the genome. The activator protein is preferably a HIF-1α or/and HIF-1β protein. If the nucleic acid sequence that is present endogenously already contains activator-binding or preferably HIF-binding nucleic acid sequences it may be sufficient to merely introduce a vector into the cell containing a nucleic acid sequence coding for an activator protein or preferably for a HIF protein which is operatively linked with an active expression control sequence in the cell and optionally a positive selection marker gene.

The expression control sequence which is linked operatively with the nucleic acid sequence coding for the activator protein can be inducible which provides an additional method for activation by suitable culture conditions such as for example by addition of hormones or heavy metals. This enables the expression of an endogenous target gene to be induced at an optimal time for the production process.

An advantage of using a constitutively active expression control sequence is that the activator protein is expressed constitutively independent of the addition of activators into the culture medium.

If the activator protein-binding nucleic acid sequence is a HIF-binding nucleic acid sequence, the expression of the target gene can for example be induced by suitable culture conditions e.g. at an $O_2$ concentration of 0.1–2%.

A further subject matter of the present invention is a vector for homologous recombination comprising
(i) at least one nucleic acid sequence which binds an activator protein,
(ii) a positive selection marker gene,
(iii) DNA sequences flanking the sequences (i) and (ii) which are homologous to a nucleic acid section in the genome of the cell in order to allow a homologous recombination.

Yet a further subject matter of the present invention is a eukaryotic cell, preferably a human cell, which is obtainable by one of the processes described above. This cell is preferably characterized in that it contains at least one heterologous, chromosomally located, activator protein/complex-binding nucleic acid fragment operatively linked with a gene that is present endogenously in the cell. Activator protein-binding nucleic acid fragments can be substituted in the genome with the aid of a site-specific recombination system as elucidated above which enables a simple identification of an optimal activator sequence for a certain target gene.

A further aspect of the invention concerns a process for testing the influence on its expression of non-coding nucleic acid sequences from the region of a target gene present endogenously in a eukaryotic cell which is characterized in that
(a) the cell is transfected with a vector comprising
 (i) a heterologous expression control sequence that is active or can be activated in the cell which is operatively linked with a reporter gene and
 (ii) non-coding nucleic acid fragments on the 5' side or/and 3' side from the region of the target gene,
(b) the cell is cultured under conditions under which the expression control sequence is active and
(c) the expression of the reporter gene is measured.

It can be simply determined with the process according to the invention how a heterologous expression control sequence has to be placed in the region of the target gene in the genome in order to achieve an optimal expression rate of the target gene and what influence the presence or the absence of 5' or/and 3' non-coding sequences from the region of the target gene has on the expression. The test vectors are preferably transiently transfected into cells and the expression of the reporter gene is determined. In this manner it is possible to rapidly and cheaply test many arrangements of a heterologous expression control sequence and a target gene or many different expression control sequences. The heterologous expression control sequences include nucleic acid sequences which can directly interact with transcription components such as transcription initiation factors or RNA polymerases and nucleic acid sequences whose influence on transcription is mediated by interactions with activators or repressors. The heterologous expression control sequence is preferably a promoter/enhancer, particularly preferably a viral promoter and most preferably a CMV promoter. The process according to the invention contributes to a strong cost reduction especially in processes which contain further complicated process steps. This is for example the case in the production of transgenic animals such as mice, sheep or cows in which it is intended to increase the expression of a particular endogenous nucleic acid sequence in a certain cell type.

The non-coding nucleic acid fragment 5' or 3' from the target gene region is preferably arranged in the vector according to it's genomic arrangement on the 5' side or 3' side of the reporter gene.

Any reporter gene known to a person skilled in the art whose expression can be detected in the cell can be used. A reporter gene is preferably used which codes for chloroamphenicol-acetyl-transferase (CAT), β-galactosidase (β-Gal) or lacZ. On the other hand it is also possible to use a reporter gene coding for a protein of interest e.g. EPO, whose expression can be detected by immunological methods e.g. ELISA.

In a preferred embodiment at least two vectors which contain different 5' or/and 3' non-coding nucleic acid fragments of the target gene are each transfected into different cells and the expression of the reporter gene in the different cells is determined with methods known to a person skilled in the art. It can be easily established with the process according to the invention which arrangement of the heterologous expression control sequence results in an optimal expression for a certain host cell.

A further aspect of the invention concerns a process for providing a DHFR-negative eukaryotic cell preferably a mammalian cell and particularly preferably a human cell which is characterized in that
(a) the cell is transfected with a first vector comprising
 (i) at least one target sequence for a site-specific recombinase,
 (ii) DNA sequences flanking sequence (i) which are homologous to a DHFR nucleic acid sequence that is present endogenously in the cell in order to allow a homologous recombination and
 (iii) optionally a positive selection marker gene and optionally a negative selection marker gene,
(b) the transfected cell is cultured under conditions under which a homologous recombination of the vector takes place and (c) the cell obtained according to step (b) is isolated.

In the process according to the invention the recombinase target sequences and the homologous sequences are selected and used as explained above.

The positive selection marker gene—if present—is arranged between the sequences that are homologous to a DHFR gene. The negative selection marker gene—if present—is arranged outside the homologous sequences.

After homologous recombination has taken place in the DHFR locus, no functional DHFR protein can be synthesized by the cell. In this case the sequences of the vector can be arranged such that the promoter of the DHFR gene is inactivated or/and such that a functional DHFR protein can no longer be synthesized due to an insertion or deletion in the coding sequence of the DHFR gene.

In order to inactivate both alleles of a DHFR gene, the cells are firstly transfected with a vector according to the invention, then selected and isolated. One allele of the DHFR gene is inactivated in these cells i.e. they are heterozygous (+/−) for the DHFR gene. Then these cells can be again transfected with a vector according to the invention which preferably contains a positive selection marker gene that is different from the first vector. After a selection step cells are obtained in which both DHFR alleles are inactivated. Alternatively an increase of the selection pressure can lead to a gene conversion and thus to an inactivation of both alleles (cf. e.g. Mortensen et al., Mol. Cell. Biol. 12 (1992), 2391–2395).

The process according to the invention provides a DHFR negative cell whose use in a gene amplification process has the advantage that it does not synthesise an endogenous DHFR protein. When a selection step is carried out to amplify a heterologous nucleic acid sequence which is coupled to a nucleic acid sequence coding for a DHFR protein, the expression product of the endogenous DHFR gene does not have an interfering influence and thus there is an increase in the efficiency of the gene amplification.

Any suitable selection marker gene that leads to a selectable phenotype can be used as a positive selection marker gene e.g. antibiotic resistance. The nucleic acid sequence coding for the positive selection marker gene is preferably a neomycin, kanamycin, geneticin or hygromycin resistance gene.

Any negative selection marker gene known to a person skilled in the art can be used, the nucleic acid sequence coding for the negative selection marker gene is preferably a thymidine kinase gene (TK) or/and hypoxanthine-guanine-phosphoribosyl transferase gene (HGPRT).

The sequence flanked by recombinase target sequences can be cleaved out of the genome of the cell by transient activation of the corresponding recombinase e.g. by (a) transfecting the cell with a vector containing a nucleic acid sequence coding for a recombinase operatively linked with an expression control sequence that is active in this cell,
(b) culturing the cell transfected in this manner under conditions under which the recombinase is expressed and is active and
(c) optionally isolating the cell.

It is not only possible with the process according to the invention to inactivate a DHFR gene but also to cut out sequences of a DHFR gene which are located between the recombinase target gene sequences as well as the introduced selection marker gene from the genome of a cell by a recombinase-mediated reaction.

If the sequence flanked by recombinase target sequences contains a positive selection marker gene, the cell containing this sequence is antibiotic resistant. Hence it can be easily selected by methods known to a person skilled in the art.

A further advantage of the DHFR-negative cell produced by the process according to the invention is that its properties can be characterized by methods known to a person skilled in the art and the cells can be subsequently used for other processes. Moreover the recombinase target sequence introduced at the DHFR gene locus enables the site-specific integration of nucleic acid sequences into the genome.

A further preferred embodiment concerns a process for introducing a heterologous DHFR gene into a eukaryotic cell which is characterized in that a DHFR-negative cell obtained by one of the processes described above (a) is transfected with a third vector comprising
  (i) optionally a positive selection marker gene which preferably differs from the positive selection marker gene of the first vector,
  (ii) a nucleic acid sequence coding for a DHFR,
  (iii) a nucleic acid sequence to be amplified coding for a protein in an expressible form in which each of the nucleic acid sequences from the partial sequences (i), (ii) and (iii) is flanked on the 5' side and 3' side by at least one recombinase target sequence
(b) the transfected cell is cultured under conditions under which the nucleic acid sequence flanked by recombinase target sequences is integrated into the recombinase target sequence that is already present in the genome of the cell and
(c) the cell obtained according to step (b) is isolated.

The positive selection marker gene, the DHFR gene and the target gene coding for the desired protein are preferably each operatively linked with an expression control sequence that is active or can be activated in the cell. A polycistronic construct with internal ribosomal binding sites is also in principle possible. The nucleic acid sequence to be amplified of the target gene should, however, be driven by a separate promoter. Particularly preferred expression control sequences are viral promoters/enhancers. A CMV promoter is most preferred for the expression of the protein.

It is advantageous to carry out the integration according to the invention of heterologous sequences into the genome of a cell in a site-specific manner and thus exclude interferences of the heterologous sequences with genomic sequences. Hence this avoids the resulting disadvantages as described further above such as unstable production clones.

In order to increase the expression rate of a heterologous nucleic acid sequence coding for a protein, it is possible to carry out an amplification step with methotrexate by known process steps.

A further subject matter of the present invention is a vector comprising
(i) optionally a positive selection marker gene,
(ii) a nucleic acid sequence coding for a DHFR and
(iii) a nucleic acid sequence in an expressible form coding for a desired protein in which each nucleic acid sequence from the partial sequences (i), (ii) and (iii) is flanked on the 5' side and 3' side by at least one recombinase target sequence.

Yet a further subject matter of the present invention is a vector for homologous recombination comprising
(i) optionally a positive selection marker gene,
(ii) at least one recombinase target sequence in each case which flanks the sequence (i) and
(iii) DNA sequences flanking the sequences (i) and (ii) which are homologous to a DHFR nucleic acid sequence that is present endogenously in a cell in order to allow a homologous recombination and (iv) optionally a negative selection marker gene outside and preferably on the 3' side of the homologous sequences (iii).

In addition the invention concerns a eukaryotic cell, preferably a human cell, obtainable by one of the processes described above. This cell is characterized in that
(a) at least one endogenous nucleic acid sequence coding for a DHFR is inactivated and preferably both endogenous alleles and
(b) at least one recombinase target sequence is integrated into the genome in the region of this nucleic acid sequence coding for DHFR.

Finally, yet a further subject matter of the invention is a eukaryotic cell, preferably a human cell, which is characterized by a heterologous nucleic acid sequence in the region of an endogenous DHFR gene locus comprising
(i) a nucleic acid sequence coding for DHFR,
(ii) a nucleic acid sequence coding for a desired protein and
(iii) at least one recombinase target sequence.

The invention is illustrated by the following examples, Figures and the sequence protocol.

FIGURE LEGENDS

FIG. 1
(A) shows a vector for the homologous recombination which is used as the first vector. HR: homologous sequence, Seq 1: first heterologous expression control sequence, R1: positive selection marker gene, loxP : loxP sequence with orientation,
(B) shows genomic sequences
   (a) after completion of the homologous recombination,
   (b) after excision of a sequence flanked by loxP sequences catalysed by a Cre recombinase,
C) shows a vector for a Cre recombinase mediated integration which contains a sequence arranged between the loxP sequences
   (c) shows genomic sequences after integration of a second vector at the loxP sequence, R2: positive selection marker gene which optionally differs from R1, Seq 2: second heterologous expression control sequence.

pHYG: control vector, pHIF-1α: a HIF-1α cDNA under the control of an SRα promoter, pARNT: a HIF-β cDNA under the control of a CMV promoter.

Figure 4:
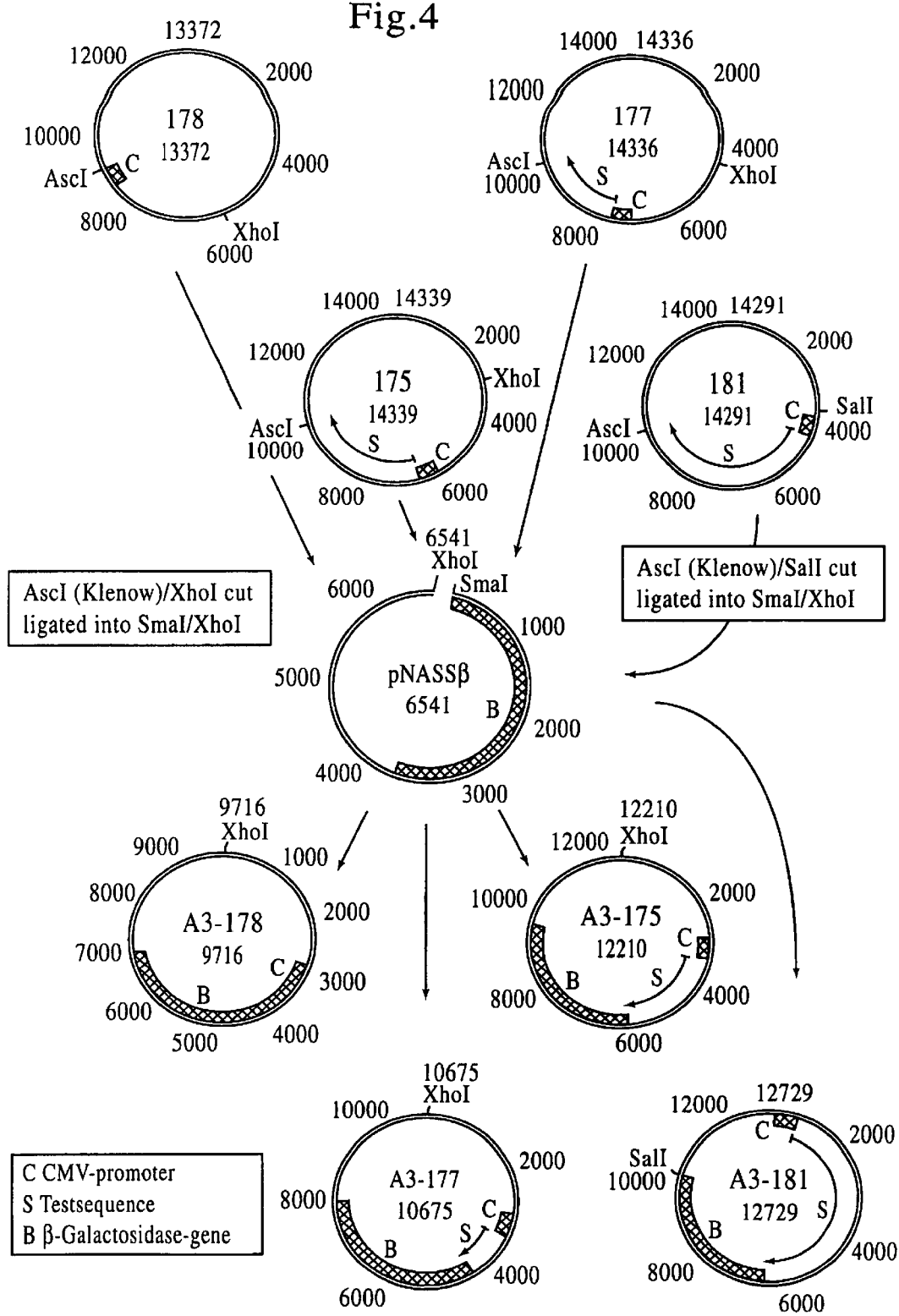

FIG. 4
shows 4 different vectors which each contain a CMV promoter (C) and the reporter gene β-galactosidase (B) in which non-coding nucleic acid fragments of the target gene (S) of different lengths have been inserted between these sequences. The length of the non-coding nucleic acid fragments is 0 kb in the vector A3-178, 2.5 kb in the vector A3-177, 3.7 kb in the vector A3-175 and 5.7 kb in the vector A3-181. The control vector pNASSβ contains the reporter gene β-galactosidase without a CMV promoter.

Figure 5:
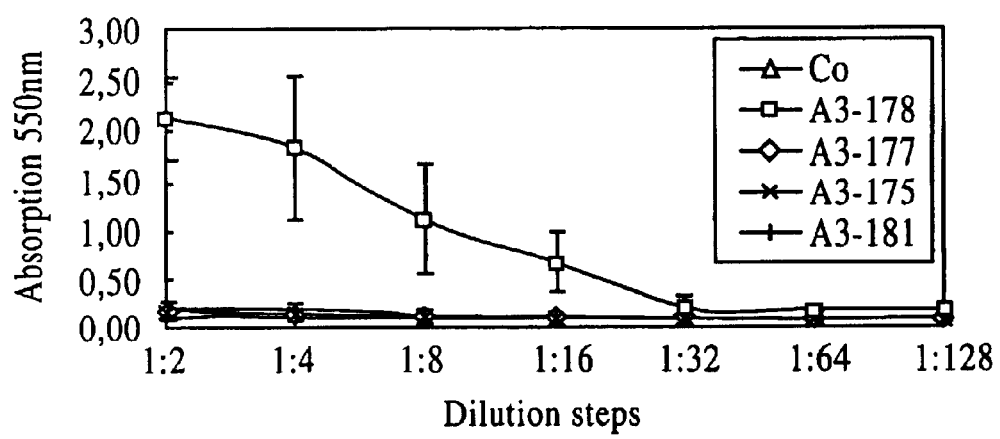

FIG. 5
shows a measurement of the expression of the reporter gene β-galactosidase after transfection of HeLa S3 cells with the vectors of FIG. 4 in a dilution series (1:2 to 1:128).

FIG. 6
(A) shows the vector pNDI for homologous recombination in a DHFR gene locus. A positive selection marker gene (Neo) is flanked by two loxP sequences. The sequences that are homologous to a DHFR gene (5', 3' DHFR region) are located on the 5' side of one of the loxP sequences and on the 3' side of the other loxP sequence.
(B) shows the vector PHDI for homologous recombination in a DHFR gene locus. A positive selection marker gene (Hyg) is flanked by two loxP sequences. The sequences that are homologous to a DHFR gene (5', 3' DHFR region) are located on the 5' side of one of the loxP sequences and on the 3' side of the other loxP sequence.

FIG. 7
(A) shows the genomic construction of a DHFR gene with exon 1, exon 2 and exon 3 as well as the introns that are located between them,
(B) shows a diagram of a target construct corresponding to the vector of FIG. 6,
(C) shows the genomic structure after completed homologous recombination of the vector for the homologous recombination in a DHFR gene. The distance between the EcoRI cleavage sites is 2.9 kb when using the vector pNDI and 3.7 kb when using the vector pHDI. Neo: neomycin, Hyg: hygromycin, kb: kilobases.

FIG. 8
shows a vector which contains a nucleic acid sequence coding for a protein X and a nucleic acid sequence coding for a DHFR protein which each include regulatory sequences and are flanked by two loxP sequences. This vector can be used for Cre recombinase catalysed integration into the genome in a loxP sequence.

SEQ ID NO.1 shows a first HIF-binding nucleotide sequence,
SEQ ID NO.2 shows a second HIF-binding nucleotide sequence
SEQ ID NO.3 shows a loxP sequence

EXAMPLES

Example 1

Figure 1:
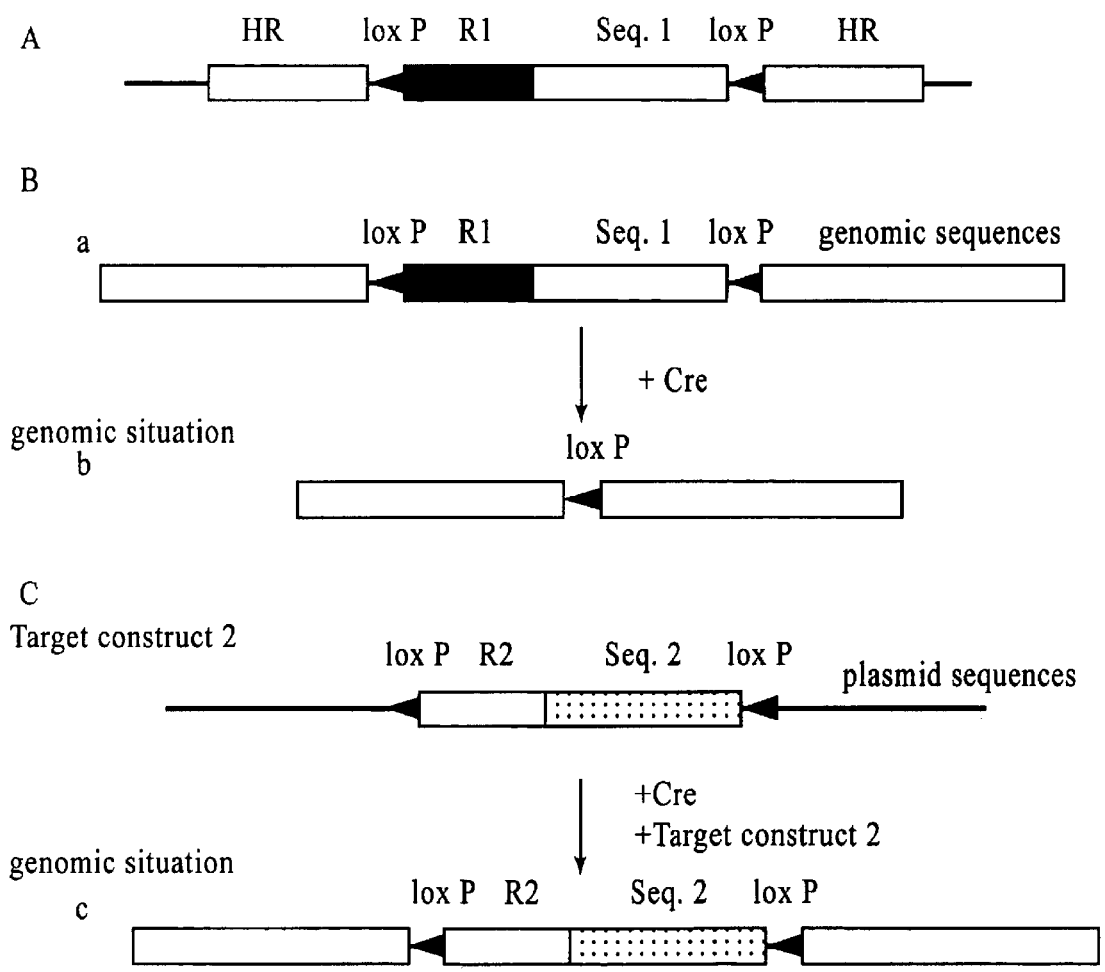
Figure 2:
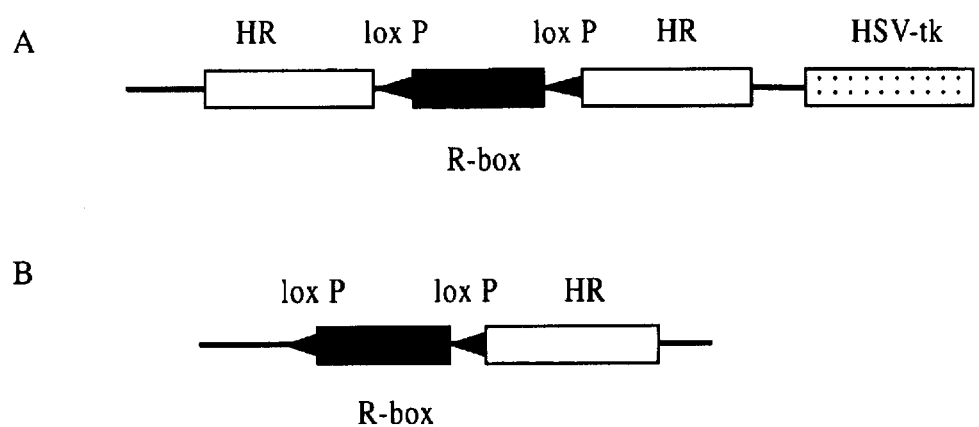
FIG. 2
(A) shows a vector for the homologous recombination HR: homologous sequence, R-box: positive and optionally negative selection marker gene, loxP : loxP sequence with orientation, HSV-tk: Herpes simplex thymidine kinase;
(B) shows a vector for the homologous recombination with one-sided homologous sequence.
Figure 3:
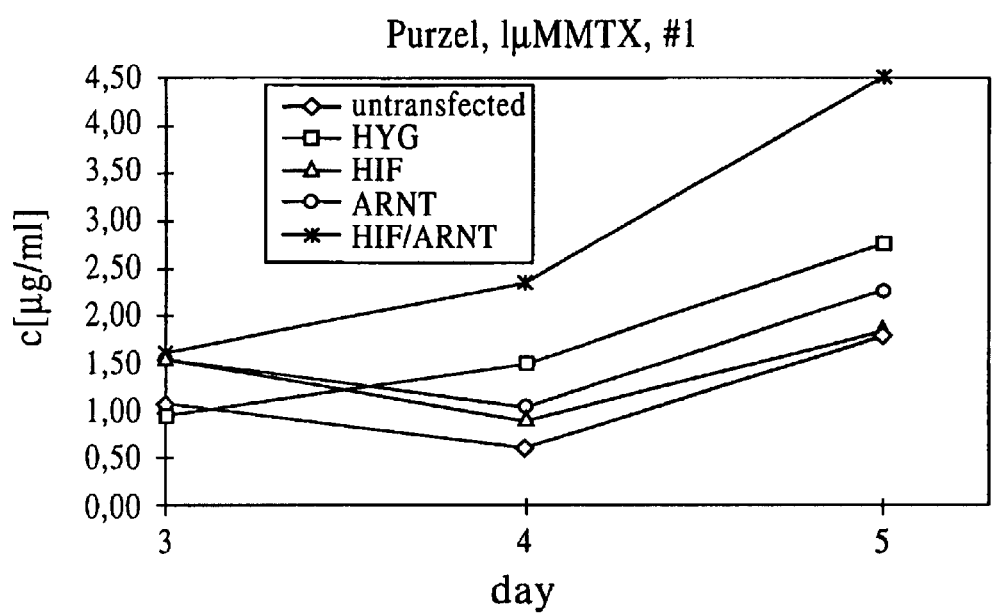
FIG. 3
shows the CMV promoter/HIF-controlled erythropoietin (EPO) expression of HeLa S3 cells which were transfected with the vectors pHYG, pHIF-1α and pARNT (pHIF-1β) and whose EPO expression was measured in the cell supernatants 3, 4 and 5 days after the transfection. as (erythropoietin concentration in μg/ml).

Expression of an Erythopoietin Gene Under the Control of a CMV Promoter and Overexpression of HIF The vectors pHYG, pHIF-1α and pARNT (cf FIG. 3) are transfected into genetically modified HeLa S3 cells. A CMV (cytomegalovirus) promoter which controls the EPO expression was introduced into the cells proximally to the erythropoietin gene (EPO) translation start of an EPO allele. The cells usually produce 1 μg erythropoietin per 24 hours per $10^7$ cells. 24 hours before transfection they are passaged at a concentration of $6 \times 10^4$ cells per 6 well plate. On the day of transfection the cells are incubated with a DNA-DOTAP mixture. The mixture contains 1.25 μg of the respective vector, 10 μl DOTAP (Boehringer Mannheim 1202375) in a final volume of 75 μl in 20 mM Hepes buffer per well. The mixture is pre-incubated for 10–15 minutes at room temperature. The cells are then incubated for 6 hours with the DNA-DOTAP in 3 ml medium per well. Subsequently the cells are washed twice with PBS buffer and cultured in complete medium for 5 days. On day 3, 4 and 5 100 μl supernatant was removed each time and analysed with an erythropoietin ELISA. The assay is completed on day 5 and the cell count is determined. The amount of erythropoietin per well is calculated relative to the same cell count (cf. FIG. 3).

The example shows that an induction of the erythropoietin gene by HIF is still possible although a heterologous expression control sequence (CMV promoter) has been introduced into the promoter region of an allele of the erythropoietin gene. The measured increase in the erythropoitin concentration indicates a synergistic effect of the hypoxia-induced factor or the hypoxia-induced factors on both alleles.

It therefore becomes evident that the expression of an endogenous nucleic acid sequence can be increased by introducing a heterologous expression control sequence. If an activator (HIF) is expressed in the cell for which binding nucleic acid sequences are present in the expression control sequence, then the expression of this gene can be further increased. If corresponding sequences are not present in this gene locus, they can be specifically introduced into the genome by the process according to the invention by means of homologous recombination.

Example 2

Optimized Arrangement of an Expression Control Sequence for Increasing the Expression of an Endogenous Nucleic Acid Sequence Sequences on the 5' side of an endogenous gene can stimulate the expression as well as have repressing properties. When a heterologous expression control sequence is introduced into the genome on the 5' side of a target gene, the expression level is influenced by the endogenous 5' sequence. In order to achieve an optimal expression of the target gene by means of a heterologous expression control sequence, this must be arranged such that the activity of the heterologous expression control sequence is not reduced by non-coding sequences on the 5' side of the target gene. A specific arrangement would be advantageous in order to achieve synergistic effects of the individual sequence elements. In order to test various arrangements of the heterologous expression control sequence i.e. in order to for example determine at which distance from the translation start of the coding sequence of the target gene the heterologous expression control sequence has to be integrated into the genome of the cell, different vectors with different 5' non-coding nucleic acid fragments of the target gene are tested (cf. FIG. 4). The vectors described in FIG. 4 are transfected into HeLa S3 cells and the expression of the reporter gene β-galactosidase is measured (cf FIG. 5). 24 hours before the assay the cells are passaged at a concentration of $1 \times 10^6$ cells per 10 centimetres petri dish. On the day of transfection the cells are incubated with a DNA-DOTAP mixture. The mixture contains 1 pmol of the respective vector (A3-178, A3-177, A3-175, A3-181 or pNASSβ, cf. FIG. 4) in 60 µl DOTAP (Boehringer Mannheim 1202375) made up to 300 µl with a 20 mM HEPES buffer solution. The mixture is incubated for 10–15 minutes at room temperature. The cells are pre-incubated for 6 hours with DNA-DOTAP in 6 ml serum-free medium per petri dish. Afterwards the cells are washed twice with PBS buffer and cultured in complete medium for 22 hours. In order to measure the β-galactosidase expression, the cells are isolated in 200 µl PBS and lysed by freezing at −20° C. and thawing. 10 µl of the lysate is diluted 1:10 with substrate (3.29 mM chlorophenol red-β-D galactopyranoside (Boehringer Mannheim 884308), 100 mM HEPES, 150 mM NaCl, 2 mM $MgCl_2$, 1% BSA, 0.1% Triton-X 100, 1% sodium azide, pH 7. The samples are diluted in 1:2 steps and incubated at 37° C. in a 96 well plate until a dark-red colour has formed. The samples are then measured at 570/580 nm, or 550 nm.

As shown in FIG. 5 the expression of the reporter gene is highest in cells that have been transfected with the vector A3-178. In this vector the heterologous expression control sequence is proximal to the translation start of the coding sequence.

Hence this method can be used to simply and rapidly determine which arrangement of a heterologous expression control sequence in the genome of a host cell has to be selected in order to achieve an optimal expression of an endogenous target gene.

Example 3

Production of DKFR-negative Cells

In a first step vectors for recombination according to the invention are prepared. These vectors are transfected into human cell lines in a second step and screened for homologous recombination events. In this manner firstly one and then the second allele for the DHFR gene can be inactivated.
DHFR Vector for Homologous Recombination The human DHFR gene is located on chromosome 5 and comprises 30 kb which are arranged in 6 exons. A 1.8 kb EcoRI fragment which contains parts of the promoter, parts of exon 2 and the complete exon 1 is used to prepare the vector for homologous recombination. Exon 1 is removed by an AapI digestion and the Neo (1.4 kb) or Hyg (2.2 kb) resistance gene is inserted into the resulting gap (0.45 kb) via linkers. These linkers contain the minimal sequence TAT TG AAG CAT ATT ACA TAC GAT ATG CTT CAA TA SEQ I.D. NO.1, (loxP sequence) in addition to the adaptor nucleotides. The linker sequences are arranged in the same orientation and the resistance gene is preferably antisense relative to the DHFR gene. After the resistance gene has been inserted, the homology region is enlarged. For this the vector is extended by the EcoRI fragments from the 3' region (6.0 kb) (FIG. 6). In this manner one obtains the target constructs pNDI (11.5 kb) and pHDI (12.3 kb) according to the invention.

After completed homologous recombination the complete exon 1 (amino acids 1–28) and parts from the promoter of the DHFR gene have been removed. The cell can now no longer express a functional DHFR protein.
Transfection of Cells The human cell lines used should not be polyploid for chromosome 5 and should not have been kept under MTX selection. In both cases more than 2 alleles would have had to been inactivated.
HeLa S3 Cells (ATCC CCL-2.2)

The cells are cultured in tissue culture flasks in RPMI 1640 medium, 10% foetal calf serum, 2 mM L-glutamine and 1 mM MEM (non-essential amino acids). The incubation is carried out at 37° C. and 5% $CO_2$. The electroporation buffer contains 20 mM Hepes, 138 mM NaCl, 5 mM KCl, 0.7 mM $Na_2HPO_4$ 6 mM D-glucose monohydrate, pH 7.0. 10 µg linearized vector DNA (pNDI) is electroporated (Biorad Gene Pulser) into $1 \times 10^7$ cells at 960 µF and 250V. After electroporation the cells are taken up in medium containing 600 µg/ml G418 (geneticin Boehringer Mannheim) and cultured. After 10 days selection (medium changed every 2 days) the positive clones are isolated and expanded.
HT1080 Cells (ATCC CCL-121)

The cells are cultured and selected as described for HeLa S3 cells using DMEM medium containing 10% foetal calf serum, 2 mM L-glutamine and 1 mM sodium pyruvate.
Namalwa Cells (ATCC CRL-1432)

This cell line is a suspension cell line and must be cultured correspondingly. The medium corresponds to that described for Hela S3 cells. After transfection the cells are distributed among forty 96-well plates. Positive clones are expanded in 48- 24- 12- and 6-well plates. The selection is carried out with 1 mg/ml G418.

Detection of the DHFR-negative (+/−) Cells

Insertion of the vector is detected by means of Southern blot analysis or by PCR. If homologous recombination has occurred correctly, a 2.9 kb band is detected after EcoR1 digestion which has been formed by the insertion of the Neo gene in addition to a 1.8 kb band which represents the intact DHFR gene (FIG. 7c). Mixed clones (unequal ratio of the band intensities in the Southern blot) are separated by single cell deposition in a FACS, subcloned and subsequently expanded, one allele of the DHFR gene is inactivated in the clones that have been identified as positive.

Production of DHFR-negative (−/−) Cells

Cell clones in which a DHFR allele (+/−) is inactivated can be subjected to a renewed homologous recombination. For this they are transfected as described above with 10 μg linearized DNA of the vector pHDI. The selection is carried out in medium containing 500 μg/ml hygromycin B (Boehringer Mannheim).

Increasing the G418 concentration in the medium increases the selection pressure on DHFR$^{+/-}$ cells and DHFR$^{-/-}$ cells are obtained. A genetic conversion leads to an interchromosomal recombination which is why the second DHFR allele is inactivated.

The DHFR$^{-/-}$ cells contain two inactivated DHFR alleles and can no longer synthesize tetrahydrofolate. Therefore thymidine, glycine and purine have to be added to the medium (supplementation). Optionally the cells are cultured in α$^-$ medium (Gibco BRL).

The DHFR$^{-/-}$ cells are detected as described above. In homozygous DHFR-negative cells no wild-type band (1.8 kb) is detectable. Cells that have been transfected with pDHI exhibit a new 3.7 kb band in EcoRI Southern blot after homologous recombination (FIG. 7c).

Use of DHFR-negative Cells (−/−)

The cells according to the invention can be used for the large-scale production of proteins. For this a vector according to the invention (according to FIG. 8) and an expression vector coding for a Cre recombinase are transfected into the DHFR$^{-/-}$ cells. The Cre recombinase removes the antibiotic resistance from the DHFR gene locus and integrates the vector according to the invention into the loxP sequence in the genome of the DHFR$^{-/-}$ cell. The cells are again antibiotic sensitive and independent of a thymidine, glycine and purine supplementation.

The selection can be achieved by using a medium without supplementation or by adding a suitable antibiotic to the culture medium. In this case the antibiotic corresponds to the resistance gene which has been removed by the Cre recombinase from the genome of the cell. If the vector integrated into the loxP sequence contains a positive selection marker gene, the selection can be carried out by adding this antibiotic to the medium.

Increasing the Production Output by Gene Amplification

In order to increase the production output of the cells for the recombinant protein, a methotrexate (MTX) selection is carried out which amplifies the DHFR gene introduced into the cell and the heterologous nucleic acid sequence coding for a protein.

In order to achieve an amplification the cells are cultured in the presence of increasing concentrations (100–1000 mM) MTX. The degree of amplification is monitored by densitometric evaluation of comparative Southern blot (before, during and after MTX addition).

The cells according to the invention obtained after the amplification step contain many copies of the introduced DHFR gene and of the inserted heterologous nucleic acid sequence at the loxP locus. They are characterized by a high production output of the heterologous nucleic acid.

What is claimed is:

1. A process for changing the expression of a nucleic acid sequence which is present endogenously in a eukaryotic cell, the method comprising
   (a) transfecting the cell with a vector comprising the following sequences
      (i) at least one sequence, which upon expression is capable of changing the expression of the nucleic acid sequence which is present endogenously in the cell, and selected from the group consisting of a heterologous expression control sequence and an amplification gene,
      (ii) a sequence encoding a positive selection marker,
      (iii) at least two target sequences for a site-specific recombinase flanking the sequences of (i) and (ii), and
      (iv) DNA sequences which flank the sequences of (i), (ii) and (iii) and are homologous to a nucleic acid section in the genome of the cell in order to allow a homologous recombination,
   (b) culturing the transfected cell under conditions under which a homologous recombination of the vector takes place,
   (c) isolating the cell obtained according to step (b), and
   (d) expressing the at least one sequence of (i) to thereby change the expression of the nucleic acid sequence which is present endogenously in the cell.

2. The process as claimed in claim 1, wherein the site-specific recombinase target sequences are loxP sequences.

3. The process as claimed in claim 1, wherein the vector further comprises a negative selection marker gene which is located outside the homologous DNA sequences (iv).

4. The process as claimed in claim 1, further comprising, after step (d), cutting the sequences of (i) and (ii) flanked by the site-specific recombinase target sequences out of the genome of the cell by transient activation of a site-specific recombinase that recognizes the target sequences.

5. A vector suitable for homologous recombination, comprising the following sequences
   (i) at least one sequence selected from the group consisting of an expression control sequence and an amplification gene each of which upon expression is capable of changing the expression of the nucleic acid sequence which is present endogenously in the cell,
   (ii) a sequence encoding a positive selection marker,
   (iii) at least two target sequences for a site-specific recombinase flanking the sequences of (i) and (ii), and
   (iv) DNA sequences which flank the sequences of (i), (ii) and (iii) and are homologous to a nucleic acid section in the genome of a cell in order to allow a homologous recombination, and
   (v) optionally a sequence encoding a negative selection marker.

6. A vector, comprising
   (i) at least one sequence selected from the group consisting of a heterologous expression control sequence and an amplification gene each of which upon expression is capable of changing the expression of the nucleic acid sequence which is present endogenously in the cell,
   (ii) a sequence encoding a positive selection marker,
   (iii) at least two recombinase target sequences flanking the sequences of (i) and (ii), and
   (iv) optionally a sequence encoding a negative selection marker.

7. A eukaryotic cell, comprising
   (a) at least one chromosomally-located sequence selected from the group consisting of a heterologous expression control sequence and an exogenous amplification gene in operative linkage with a nucleic acid sequence which is present endogenously in the cell, and
   (b) recombinase target sequences flanking the sequence (a).

8. The eukaryotic cell of claim 7, wherein the cell is a human cell.

9. A process for changing the expression of a nucleic acid sequence which is present endogenously in a eukaryotic cell, the method comprising
   (a) transfecting the cell with a vector comprising
      (i) at least one nucleic acid sequence which binds an activator protein,
      (ii) a sequence encoding a positive selection marker, and
      (iii) DNA sequences which flank the sequences of (i) and (ii) and are homologous to a nucleic acid section in the genome of the cell in order to allow a homologous recombination,
   (b) culturing the transfected cell under conditions under which a homologous recombination of the vector takes place,
   (c) isolating the cell obtained according to step (b), and
   (d) expressing the sequence of (i) under conditions under which the activator protein is bound thereby changing the expression of the nucleic acid sequence which is present endogenously in the cell.

10. The process as claimed in claim 9, wherein the sequence (i) is a hypoxia-inducible factor-binding nucleic acid sequence.

11. A eukaryotic cell obtainable by the process as claimed in claim 9.

12. The eukaryotic cell of claim 11, wherein the cell is a human cell.

13. A vector suitable for homologous recombination, comprising
   (i) at least one nucleic acid sequence which binds an activator protein,
   (ii) a positive selection marker gene, and
   (iii) DNA sequences which flank the sequences (i) and (ii) and are homologous to a nucleic acid section in the genome of a cell in order to allow a homologous recombination.

14. A eukaryotic cell, comprising at least one chromosomally-located exogenous nucleic acid sequence which binds an activator protein/activator protein complex which is operatively linked with a gene which is present endogenously in the cell.

15. The eukaryotic cell of claim 14, wherein the cell is a human cell.

16. A process for testing the influence of non-coding nucleic acid sequences from the region of a target gene present endogenously in a eukaryotic cell on its expression, the process comprising
   (a) transfecting the cell with a vector comprising
      (i) a heterologous expression control sequence which is active or can be activated in the cell and is operatively linked with a reporter gene, and
      (ii) non-coding nucleic acid sequences on the 5'-side and/or the 3'-side from the region of the target gene,
   (b) culturing the cell under conditions under which the expression control sequence is active, and
   (c) measuring the expression of the reporter gene to determine the influence of the non-coding nucleic acid sequences on the expression of the target gene.

17. A process for obtaining a DHFR-negative eukaryotic cell, the process comprising
  (a) transfecting a DHFR-positive cell with a first vector comprising
    (i) at least one DHFR-negative target sequence for a site-specific recombinase;
    (ii) DNA sequences which flank sequence (i) and are homologous to a DHFR nucleic acid sequence which is present endogenously in the cell in order to allow a homologous recombination,
    (iii) optionally a sequence encoding a first positive selection marker, and
    (iv) optionally a sequence encoding a negative selection marker,
  (b) culturing the transfected cell under conditions under which a homologous recombination of the vector takes place thereby incorporating the DHFR-negative target sequence into the DHFR-positive cell to create a DHFR-negative cell, and
  (c) isolating the cells obtained according to step (b) to obtain a DHFR-negative eukaryotic cell.

18. A process for obtaining a eukaryotic cell containing a nucleic acid sequence to be amplified and a heterologous DHFR gene, the process comprising
  (a) obtaining a DHFR-negative eukaryotic cell by the process as claimed in claim 17, (b) transfecting the cell of step (a) with a second vector comprising
    (i) a nucleic acid sequence coding for a DHFR,
    (ii) a nucleic acid sequence to be amplified which codes for a protein in an expressible form,
    (iii) optionally a sequence encoding a second positive selection marker, and
    (iv) at least two recombinase target sequences flanking the sequences of (i), (ii) and (iii), if present,
  (c) culturing the transfected cell under conditions under which the sequences of (i), (ii) and (iii), if present, are integrated into the recombinase target sequence that is already present in the genome of the cell, and
  (d) isolating the cell obtained according to step (c) to obtain a eukaryotic cell containing a nucleic acid sequence to be amplified and a heterologous DHFR gene.

19. The process of claim 18, wherein the second positive selection marker gene differs from the first positive selection marker gene.

20. A vector, comprising
  (i) a nucleic acid sequence coding for a DHFR,
  (ii) a nucleic acid sequence to be amplified which codes for a protein in an expressible form,
  (iii) optionally a sequence encoding a positive selection marker, and
  (iv) at least two recombinase target sequences flanking the sequences of (i), (ii) and (iii), if present.

21. A vector suitable for homologous recombination, comprising
  (i) optionally a sequence encoding a positive selection marker,
  (ii) at least one recombinase target sequence which flanks the sequence of (i), if present,
  (iii) DNA sequences which flank the sequences of (i), if present, and (ii) and which are homologous to a DHFR nucleic acid sequence which is present endogenously in a cell in order to allow a homologous recombination, and
  (iv) optionally a sequence encoding a negative selection marker which is outside the homologous DNA sequences (iii).

22. A mammalian cell, comprising
  (a) at least one inactivated endogenous nucleic acid sequence coding for a DHFR, and
  (b) at least one recombinase target sequence which is integrated into the genome in the region of the sequence (a).

23. The mammalian cell of claim 22, wherein the cell is a human cell.

24. A mammalian cell, comprising a heterologous nucleic acid sequence in the region of an endogenous DHFR gene locus, the heterologous sequence comprising
  (i) a nucleic acid sequence coding for a DHFR,
  (ii) a nucleic acid sequence coding for a desired protein, and
  (iii) at least one recombinase target sequence.

* * * * *

SEQUENCE LISTING

```
<160> NUMBER OF SEQ ID NOS: 3

<210> SEQ ID NO 1
<211> LENGTH: 53
<212> TYPE: DNA
<213> ORGANISM: Homo sapiens

<400> SEQUENCE: 1
cctctcctct aggcccgtgg ggctggccct gcaccgccga gcttcccggg atg          53

<210> SEQ ID NO 2
<211> LENGTH: 43
<212> TYPE: DNA
<213> ORGANISM: Homo sapiens

<400> SEQUENCE: 2
ctacgtgctg tctcacacag cctgtctgac ctctcgaccc tac                     43

<210> SEQ ID NO 3
<211> LENGTH: 34
<212> TYPE: DNA
<213> ORGANISM: Homo sapiens

<400> SEQUENCE: 3
tattgaagca tattacatac gatatgcttc aata                               34
```